(12) United States Patent
Marché et al.

(10) Patent No.: US 11,938,947 B2
(45) Date of Patent: Mar. 26, 2024

(54) SYSTEMS AND METHODS FOR SENSOR-BASED OPERATOR FATIGUE MANAGEMENT

(71) Applicant: Honeywell International s.r.o., Prague (CZ)

(72) Inventors: Stéphane Marché, Toulouse (FR); Sander Roosendaal, Brno (CZ)

(73) Assignee: Honeywell International s.r.o., Prague (CZ)

( * ) Notice: Subject to any disclaimer, the term of this patent is extended or adjusted under 35 U.S.C. 154(b) by 84 days.

(21) Appl. No.: 17/647,096

(22) Filed: Jan. 5, 2022

(65) Prior Publication Data

US 2023/0211789 A1   Jul. 6, 2023

(51) Int. Cl.
*B60W 40/08* (2012.01)
*A61B 5/00* (2006.01)
(Continued)

(52) U.S. Cl.
CPC .............. *B60W 40/08* (2013.01); *A61B 5/18* (2013.01); *A61B 5/6802* (2013.01); *B60W 50/14* (2013.01);
(Continued)

(58) Field of Classification Search
CPC ................. B60W 40/08; B60W 50/14; B60W 2040/0827; B60W 2040/0872;
(Continued)

(56) References Cited

U.S. PATENT DOCUMENTS 10,244,965 B1 *   4/2019   Gibson ................... G16H 80/00
2006/0200008 A1 *   9/2006   Moore-Ede ............ B60K 28/06
128/920
(Continued)

FOREIGN PATENT DOCUMENTS

WO   2006/000166 A1   1/2006
WO   2016034473 A1   3/2016

OTHER PUBLICATIONS

"Collins Aerospace and Seeing Machines work together to combat pilot fatigue" Nov. 15, 2021. https://www.collinsaerospace.com/newsroom/News/2021/11/Collins-and-Seeing-Machines-work-together-to-combat-pilot-fatigue.
(Continued)

*Primary Examiner* — Omar Casillashernandez
(74) *Attorney, Agent, or Firm* — Alston & Bird LLP (57) ABSTRACT

A system for monitoring a fatigue level of an operator of a vehicle includes a sensor configured to generate a signal indicative of a physiological state of the operator; a display for the operator; and a controller to: receive, from the sensor, the signal; determine the fatigue level of the operator by analyzing the received signal using an algorithm developed using operator fatigue statistics; generate a real-time fatigue report for the operator based on the determined fatigue level of the operator; transmit the generated real-time fatigue report to the display for the operator for display to the operator, and a display for a dispatcher for the vehicle for display to the dispatcher; generate an anonymized version of the real-time fatigue report; and transmit the anonymized version of the real-time fatigue report to a cloud for access by remote users.

6 Claims, 4 Drawing Sheets

(51) Int. Cl.
*A61B 5/18* (2006.01)
*B60W 50/14* (2020.01)
*G06N 20/00* (2019.01)
*G06Q 10/0631* (2023.01)
*G07C 5/00* (2006.01)
*G07C 5/08* (2006.01)

(52) U.S. Cl.
CPC ....... *G06N 20/00* (2019.01); *G06Q 10/06312* (2013.01); *G07C 5/008* (2013.01); *G07C 5/0825* (2013.01); *B60W 2040/0827* (2013.01); *B60W 2040/0872* (2013.01); *B60W 2050/146* (2013.01); *B60W 2540/221* (2020.02); *B60W 2540/229* (2020.02); *B60W 2556/45* (2020.02)

(58) Field of Classification Search
CPC ..... B60W 2050/146; B60W 2540/221; B60W 2540/229; B60W 2556/45; A61B 5/18; A61B 5/6802; G06N 20/00; G06Q 10/06312; G07C 5/008; G07C 5/0825
USPC .......................................................... 340/576
See application file for complete search history.

(56) References Cited

U.S. PATENT DOCUMENTS

| | | | |
|---|---|---|---|
| 2007/0296601 A1* | 12/2007 | Sultan | A61B 5/082 |
| | | | 340/576 |
| 2016/0090097 A1 | 3/2016 | Grube et al. | |
| 2017/0010667 A1* | 1/2017 | Tanaka | G06F 3/011 |
| 2018/0274927 A1* | 9/2018 | Epperlein | G01C 21/3415 |
| 2019/0087906 A1* | 3/2019 | Fields | G08B 13/18 |
| 2021/0403004 A1* | 12/2021 | Alvarez | G06F 18/214 |
| 2022/0401739 A1* | 12/2022 | Srivastava | A61N 1/36139 |

OTHER PUBLICATIONS

Hourlier et al "An objective Human fatigue monitoring solution for Fatigue Risk Management or Reduced Crew Operations", Thales Avionics at DASC conference Oct. 5-8, 2021 (4 pages).
Extended European search report and search opinion dated May 3, 2023 for EP Application No. 22205073, 9 page(s).

* cited by examiner

SYSTEMS AND METHODS FOR SENSOR-BASED OPERATOR FATIGUE MANAGEMENT

GOVERNMENT CONTRACT

The project leading to this application has received funding from the Clean Sky 2 Joint Undertaking under the European Union's Horizon 2020 research and innovation programme under grant agreement No 807097.

TECHNICAL FIELD

Various embodiments of the present disclosure relate generally to sensor-based operator fatigue management and, more particularly, to monitoring and managing a fatigue level of an operator using sensors and anonymized data.

BACKGROUND

Operator fatigue contributes to a significant percentage of incidents, accidents, and other disruptions involving human-operated equipment, which can inconvenience customers and bring significant cost to carriers, such as airlines, for example. Current processes for quantifying and mitigating operator fatigue typically build operator schedules using empirical tools based on theoretical models and subjective operator reports. Such theoretical models may provide an average fatigue level for an average operator in a given situation. However, current processes do not provide precise objective information of a level of fatigue of an individual operator, and use this objective information to manage a level of fatigue for an individual operator. Moreover, existing systems cannot manage both operator-specific and anonymized fatigue information for various use cases.

The present disclosure is directed to overcoming one or more of these above-referenced challenges.

SUMMARY OF THE DISCLOSURE

In some aspects, the techniques described herein relate to a system for monitoring a fatigue level of an operator of a vehicle, the system including: at least one sensor configured to generate a signal indicative of a physiological state of the operator; a display for the operator; and one or more controllers configured to: receive, from the at least one sensor, the signal indicative of the physiological state of the operator; determine the fatigue level of the operator by analyzing the received signal using an algorithm developed using operator fatigue statistics; generate a real-time fatigue report for the operator based on the determined fatigue level of the operator; transmit the generated real-time fatigue report to (1) the display for the operator for display to the operator, and (2) a display for a dispatcher for the vehicle for display to the dispatcher; generate an anonymized version of the real-time fatigue report; and transmit the anonymized version of the real-time fatigue report to a cloud for access by remote users.

In some aspects, the techniques described herein relate to a system, wherein the one or more controllers are further configured to: transmit the anonymized version of the real-time fatigue report to an operator fatigue statistics database; and train a machine learning algorithm using an operator fatigue statistics database including the anonymized version of the real-time fatigue report, as the algorithm.

In some aspects, the techniques described herein relate to a system, wherein the anonymized version of the real-time fatigue report is generated after operation of the vehicle is completed by the operator.

In some aspects, the techniques described herein relate to a system, wherein the one or more controllers are further configured to: optimize a schedule for the operator to operate the vehicle, using the operator fatigue statistics database.

In some aspects, the techniques described herein relate to a system, wherein the one or more controllers are further configured to: determine a sleep level of the operator by analyzing the received signal using an algorithm developed using the operator fatigue statistics.

In some aspects, the techniques described herein relate to a system, wherein the real-time fatigue report includes the determined sleep level of the operator.

In some aspects, the techniques described herein relate to a system, wherein the fatigue level is provided as a number from 1 to 5.

In some aspects, the techniques described herein relate to a method for monitoring a fatigue level of an operator of a vehicle, the method including: performing, by one or more controllers, operations including: receiving, from at least one sensor, a signal indicative of a physiological state of the operator; determining the fatigue level of the operator by analyzing the received signal using an algorithm developed using operator fatigue statistics; generating a real-time fatigue report for the operator based on the determined fatigue level of the operator; transmitting the generated real-time fatigue report to (1) a display for the operator for display to the operator, and (2) a display for a dispatcher for the vehicle for display to the dispatcher; generating an anonymized version of the real-time fatigue report; and transmitting the anonymized version of the real-time fatigue report to a cloud for access by remote users.

In some aspects, the techniques described herein relate to a method, wherein the operations further include: transmitting the anonymized version of the real-time fatigue report to an operator fatigue statistics database; and training a machine learning algorithm using an operator fatigue statistics database including the anonymized version of the real-time fatigue report, as the algorithm.

In some aspects, the techniques described herein relate to a method, wherein the anonymized version of the real-time fatigue report is generated after operation of the vehicle is completed by the operator.

In some aspects, the techniques described herein relate to a method, wherein the operations further include: optimizing a schedule for the operator to operate the vehicle, using the operator fatigue statistics database.

In some aspects, the techniques described herein relate to a method, wherein the operations further include: determining a sleep level of the operator by analyzing the received signal using an algorithm developed using the operator fatigue statistics.

In some aspects, the techniques described herein relate to a method, wherein the real-time fatigue report includes the determined sleep level of the operator.

In some aspects, the techniques described herein relate to a method, wherein the fatigue level is provided as a number from 1 to 5.

In some aspects, the techniques described herein relate to a non-transitory computer-readable medium storing instructions, that when executed by one or more controllers, perform a method for monitoring a fatigue level of an operator of a vehicle, the method including: receiving, from at least one sensor, a signal indicative of a physiological state of the operator; determining the fatigue level of the operator by analyzing the received signal using an algorithm developed using operator fatigue statistics; generating a real-time fatigue report for the operator based on the determined fatigue level of the operator; transmitting the generated real-time fatigue report to (1) a display for the operator for display to the operator, and (2) a display for a dispatcher for the vehicle for display to the dispatcher; generating an anonymized version of the real-time fatigue report; and transmitting the anonymized version of the real-time fatigue report to a cloud for access by remote users.

In some aspects, the techniques described herein relate to a non-transitory computer-readable medium, wherein the at least one sensor includes one or more of wristbands, pressure pads, or cameras.

In some aspects, the techniques described herein relate to a non-transitory computer-readable medium, wherein the one or more controllers are provided as a wearable system by the operator.

In some aspects, the techniques described herein relate to a non-transitory computer-readable medium, wherein the one or more controllers are provided as an integrated system of the vehicle.

In some aspects, the techniques described herein relate to a non-transitory computer-readable medium, wherein the method further includes: determining a sleep level of the operator by analyzing the received signal using an algorithm developed using the operator fatigue statistics.

In some aspects, the techniques described herein relate to a non-transitory computer-readable medium, wherein the real-time fatigue report includes the determined sleep level of the operator provided as a number from 1 to 5.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims. As will be apparent from the embodiments below, an advantage to the disclosed systems and methods is for an operational center to detect severe fatigue and find a replacement operator, thus reducing significantly the inconvenience and cost. By accessing more precise information on an actual level of fatigue by the disclosed systems and methods, operators may be more likely to extend duty time in some exceptional situations when time limits would have a severe operational impact. By accessing more precise information on an actual level of fatigue by the disclosed systems and methods, operators may be more likely to realize they should stop operating a vehicle, thus avoiding a risk of accident. Additionally, by monitoring a quality of sleep by the disclosed systems and methods, resting times for operators may be optimized during long range operations, which may optimize operator usage via optimized scheduling.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Various embodiments of the present disclosure relate generally to sensor-based operator fatigue management and, more particularly, to monitoring and managing a fatigue level of an operator using sensors and anonymized data.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section.

Various embodiments of the present disclosure relate generally to improving the level of safety and cost efficiency of operator-performed tasks by monitoring and managing a fatigue level of an operator. For example, in the airline industry, NTSB has identified that fatigue contributes to at least 20% of incidents and accidents. Fatigue is also a cause of flight disruptions. Addressing those situations before they occur would be a benefit to both airlines and travelers.

Using the airline industry as an example, various embodiments of the present disclosure may feature a set of sensors installed in a cockpit of an aircraft to acquire biometric data from a pilot and detect various conditions including fatigue. Various embodiments may include tools for a ground dispatcher to remotely monitor the pilot's state and a system on the ground may automatically generate fatigue diagnostics and prognostics to define future flight schedules by taking the pilot's individual risk of fatigue into account. This differs from the current processes where airlines build pilot schedules using empirical tools based on theoretical model and subjective pilot reports.

Currently, when a pilot reports significant fatigue, this can lead to cancelling the next flight. Various embodiments of the present disclosure may enable an airline operational center to detect severe fatigue early, allowing managers to find a replacement crew. By accessing objective and precise information on a pilot's actual level of fatigue, pilots are more likely to extend duty time in some exceptional situations when flight time limits may have a severe operational impact. Various embodiments of the present disclosure may also monitor sleep, which has the potential to optimize crew resting times during long range operations for optimizing pilot flight schedules.

Various embodiments of the present disclosure may be easy to install for airline maintenance engineers due to the use of wireless technologies and may be performed during a regular aircraft check. Additionally, by using datalink tools for airline operation centers, various embodiments of the present disclosure may provide a fatigue management application fully integrated in the dispatcher working position.

Although the airline industry is used an example above, the disclosure is not limited thereto. Various embodiments of the present disclosure may apply to any vehicle or other equipment that requires operation by an operator.

As will be apparent from the embodiments below, an advantage to the disclosed systems and methods is for an operational center to detect severe fatigue and find a replacement operator, thus reducing significantly the inconvenience and cost. By accessing more precise information on an actual level of fatigue by the disclosed systems and methods, operators may be more likely to extend duty time in some exceptional situations when time limits would have a severe operational impact. By accessing more precise information on an actual level of fatigue by the disclosed systems and methods, operators may be more likely to realize they should stop operating a vehicle, thus avoiding a risk of accident. Additionally, by monitoring a quality of sleep by the disclosed systems and methods, resting times for operators may be optimized during long range operations, which may optimize operator usage via optimized scheduling. Embodiments below may detect, earlier than conventional systems, that an operator has reached a level of fatigue that is not sustainable. Embodiments below may predict if the operator will recover from the current level of fatigue depending on a trend determined during observation.

Figure 1:
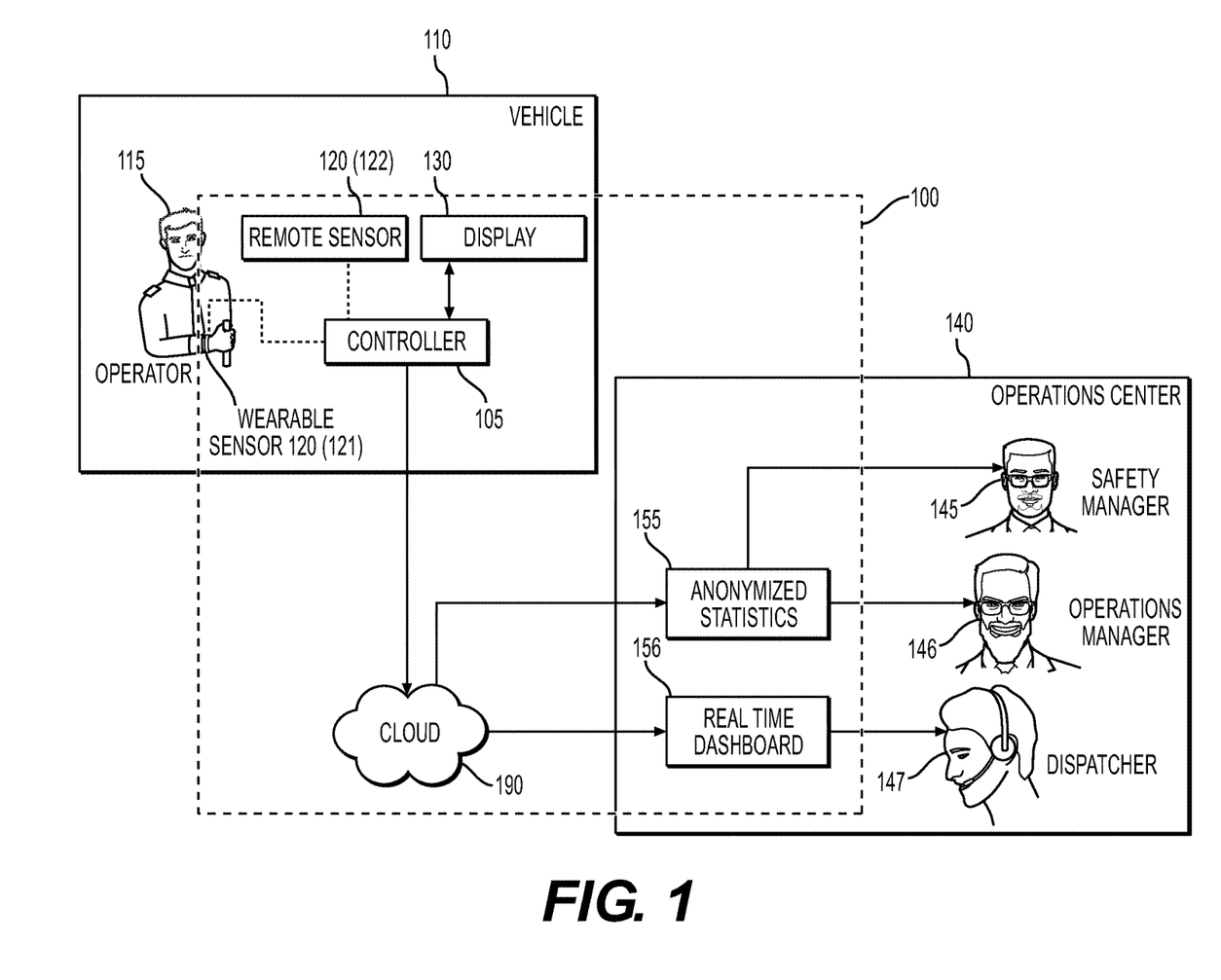
FIG. 1 depicts an exemplary system infrastructure for monitoring and managing a fatigue level of an operator using sensors and anonymized data, according to one or more embodiments.

Any suitable system infrastructure may be put into place to implement the present disclosure. FIG. 1 and the following discussion provide a brief, general description of a suitable computing environment in which the present disclosure may be implemented. In one embodiment, any of the disclosed systems, methods, and/or graphical user interfaces may be executed by or implemented by a computing system consistent with or similar to that depicted in FIG. 1. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

FIG. 1 depicts an exemplary system infrastructure for a system 100 for monitoring and managing a fatigue level of an operator using sensors and anonymized data, according to one or more embodiments. System 100 may include controller 105, at least one sensor 120, and display 130.

As shown in FIG. 1, an operator 115 may operate a vehicle 110. Vehicle 110 may be any type of motor vehicle, train, tram, ship, boat, amphibious vehicle, hovercraft, aircraft, airplane, helicopter, balloon, powered airship, or spacecraft, for example. Operator 115 may operate the vehicle from a position onboard the vehicle 110. While the present embodiments are described with reference to a vehicle 110, it should be appreciated that the systems and methods are also applicable to an operator's use of any equipment, such as heavy equipment, computer equipment, aircraft controller equipment, power plant equipment, drone controls, or any other sensitive or high-stakes equipment. Additionally, if the vehicle 110 is an unmanned aerial vehicle, for example, operator 115 may operate the vehicle 110 from a remote position outside the vehicle 110. However, the disclosure is not limited to the examples above, and may apply to any vehicle 110 or other equipment that requires operation by an operator 115.

Operator 115 may wear a wearable sensor 121, which may be one or more of a wristband, headband, or electrophysiological monitoring, for example. Wearable sensor 121 may be configured to generate a signal indicative of a physiological state or biometric data of the operator 115.

Remote sensor 122 may be placed in vehicle 110, and may be a camera configured to view an operator, or a pressure pad in an operator seat that is configured to measure a sitting position of the operator, for example. Remote sensor 122 may be configured to generate a signal indicative of a physiological state or biometric data of the operator 115.

Although system 100 is described above as including wearable sensor 121 and remote sensor 122, the disclosure is not limited thereto. For example, wearable sensor 121 and remote sensor 122 may be provided as a single sensor that is either wearable or remote, or both wearable and remote, or as more than two sensors in any combination of wearable and/or remote. For example, wearable sensor 121 and remote sensor 122 may be provided as four wristbands, two pressure pads, and three cameras. Accordingly, for the purposes of this disclosure, any combination of wearable sensor 121 and/or remote sensor 122 will be referred to as sensor 120.

System 100 may be placed in vehicle 110 as a portable system, or as an integrated system with vehicle 110, or may be remote from vehicle 110. Controller 105 may receive a signal from sensor 120 and determine a fatigue level of the operator 115 by analyzing the received signal using an algorithm, such as a machine learning algorithm trained on an operator fatigue statistics database, for example.

The machine learning algorithm that may be useful and effective for the analysis is a neural network, which is a type of supervised machine learning. However, other machine learning techniques and frameworks may be used to perform the methods contemplated by the present disclosure. For example, the systems and methods may be realized using other types of supervised machine learning, such as regression problems, random forest, etc., using unsupervised machine learning such as cluster algorithms, principal component analysis (PCA), etc., and/or using reinforcement learning. The algorithm may alternatively or additionally be rule-based.

Supervised machine learning may be useful when system 100 is certified, and the machine learning algorithm may be certified and closed so that no further updates are applied. However, the disclosure is not limited thereto, and the machine learning algorithm may be trained in a supervised or unsupervised manner with the operator fatigue statistics database on a periodic or ongoing basis.

The fatigue level may be provided as a drowsiness level of the operator 115 based on a heart rate, respiration rate, or movement of the operator 115, for example, provided by sensor 120. The drowsiness level may be provided as a number from 1 to 5, for example, although the disclosure is not limited thereto. The fatigue level may be provided as a sleep level of the operator 115 based on the signal from sensor 120. The sleep level may be provided as a number from 1 to 5, for example, although the disclosure is not limited thereto.

Controller 105 may generate a real-time fatigue report for the operator 115 based on the determined fatigue level of the operator 115. Controller 105 may generate an anonymized version of the real-time fatigue report for access in the cloud 190 by remote users. Controller 105 may transmit the anonymized version of the real-time fatigue report to the operator fatigue statistics database.

Controller 105 may generate a real-time fatigue report for the operator 115 during operation of the vehicle 110. The real-time fatigue report may be provided as a real-time report only so that personal data from operator 115 is not stored. Controller 105 may generate the anonymized version of the real-time fatigue report following operation of the vehicle 110, and ensure any identifying data for operator 115 is anonymized so that an identity of operator 115 is de-correlated from any associated fatigue data.

Display 130 may be placed in vehicle 110 as a portable system, as an integrated system with vehicle 110, or may be remote from vehicle 110. Controller 105 may provide the real-time fatigue report to display 130 for display to the operator 115.

The controller 105, sensor 120, and display 130 may be provided as separate components, or may be provided as any integrated combination. For example, the controller 105, sensor 120, and display 130 may be provided as a combination in a smartwatch or mobile phone.

Controller 105 may provide the real-time fatigue report and the anonymized version of the real-time fatigue report to cloud 190. Cloud 190 may provide the real-time fatigue report and the anonymized version of the real-time fatigue report to operations center 140 in the form of anonymized statistics 155 and real-time dashboard 156. The anonymized statistics 155 may be viewed by a safety manager 145 and an operations manager 146. The real-time fatigue report may be viewed by a dispatcher 147 as part of real-time dashboard 156.

The anonymized version of the real-time fatigue report may be used along with other anonymized versions of real-time fatigue reports for other operators to optimize a schedule for operators including operator 115 to reduce a fatigue of the operators during operation of vehicle 110.

Figure 2:
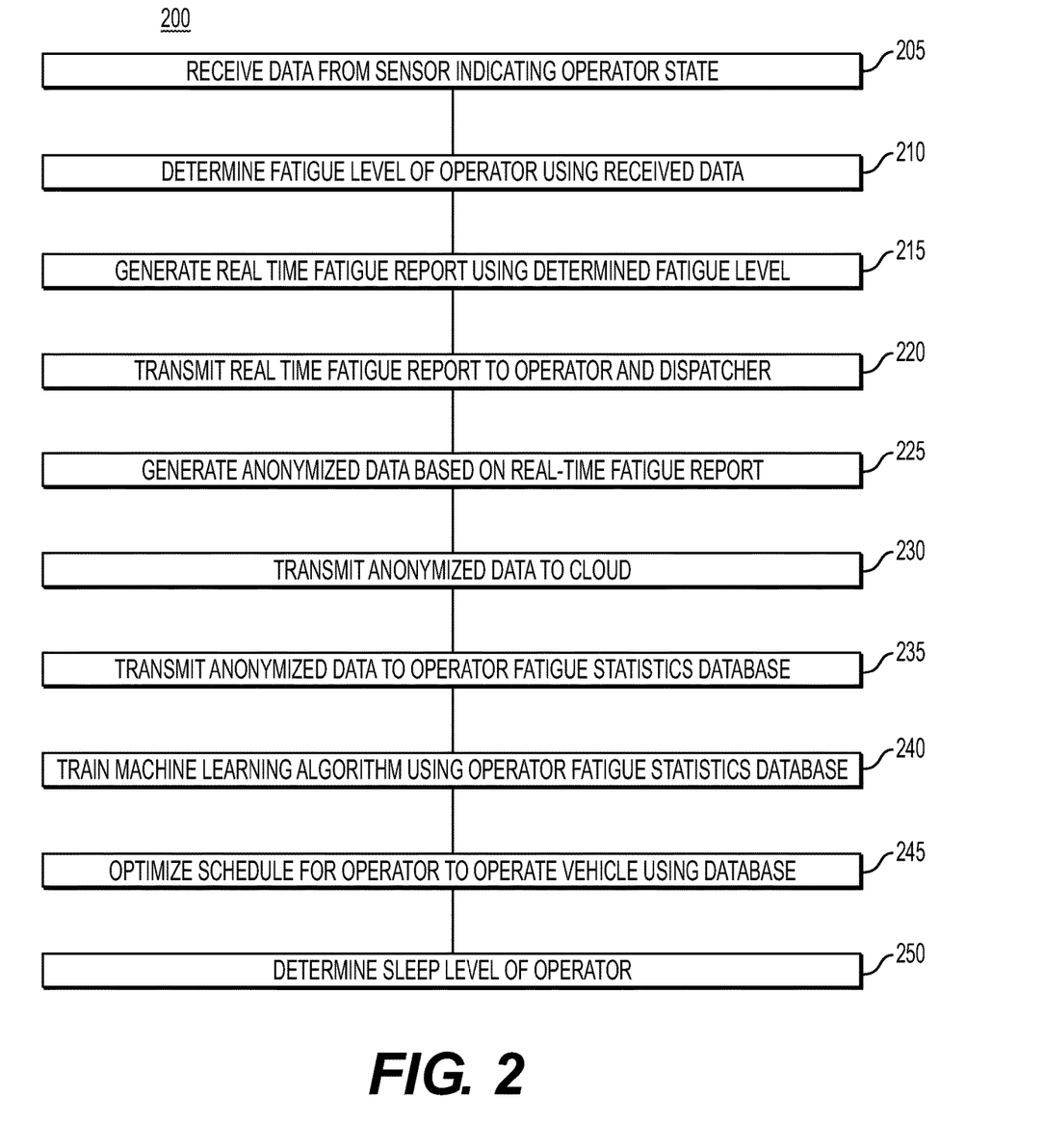
FIG. 2 depicts a flowchart of a method of monitoring and managing a fatigue level of an operator using sensors and anonymized data, according to one or more embodiments.

FIG. 2 depicts a flowchart of a method 200 of monitoring and managing a fatigue level of an operator using sensors and anonymized data, according to one or more embodiments.

Controller 105 may receive, from at least one sensor 120, a signal indicative of a physiological state of the operator 115 (operation 205). Controller 105 may determine the fatigue level of the operator 115 by analyzing the received signal using a machine learning algorithm trained on an operator fatigue statistics database (operation 210). Controller 105 may generate a real-time fatigue report for the operator 115 based on the determined fatigue level of the operator 115 (operation 215). Controller 105 may transmit the generated real-time fatigue report to (1) a display 130 for the operator 115 for display to the operator 115, and (2) a real-time dashboard 156 for a dispatcher 147 for the vehicle 110 for display to the dispatcher 147 (operation 220).

Controller 105 may generate an anonymized version of the real-time fatigue report (operation 225), and transmit the anonymized version of the real-time fatigue report to a cloud 190 for access by remote users (operation 230). The remote users may include a safety manager 145 and an operations manager 146 viewing the anonymized version of the real-time fatigue report as anonymized statistics 155 in operations center 140.

Controller 105 may transmit the anonymized version of the real-time fatigue report to the operator fatigue statistics database, which may be stored in cloud 190 (operation 235). Controller 105 may train the machine learning algorithm using the operator fatigue statistics database including the anonymized version of the real-time fatigue report (operation 240).

The anonymized version of the real-time fatigue report may be generated by controller 105 after operation of the vehicle 110 is completed by the operator 115. Controller 105 may optimize a schedule for the operator 115 to operate the vehicle 110, using the operator fatigue statistics database (operation 245).

Controller 105 may determine a sleep level of the operator 115 by analyzing the received signal using a machine learning algorithm trained on the operator fatigue statistics database (operation 250). The real-time fatigue report may include the determined sleep level of the operator 115. The fatigue level may be provided as a number from 1 to 5.

Figure 3:
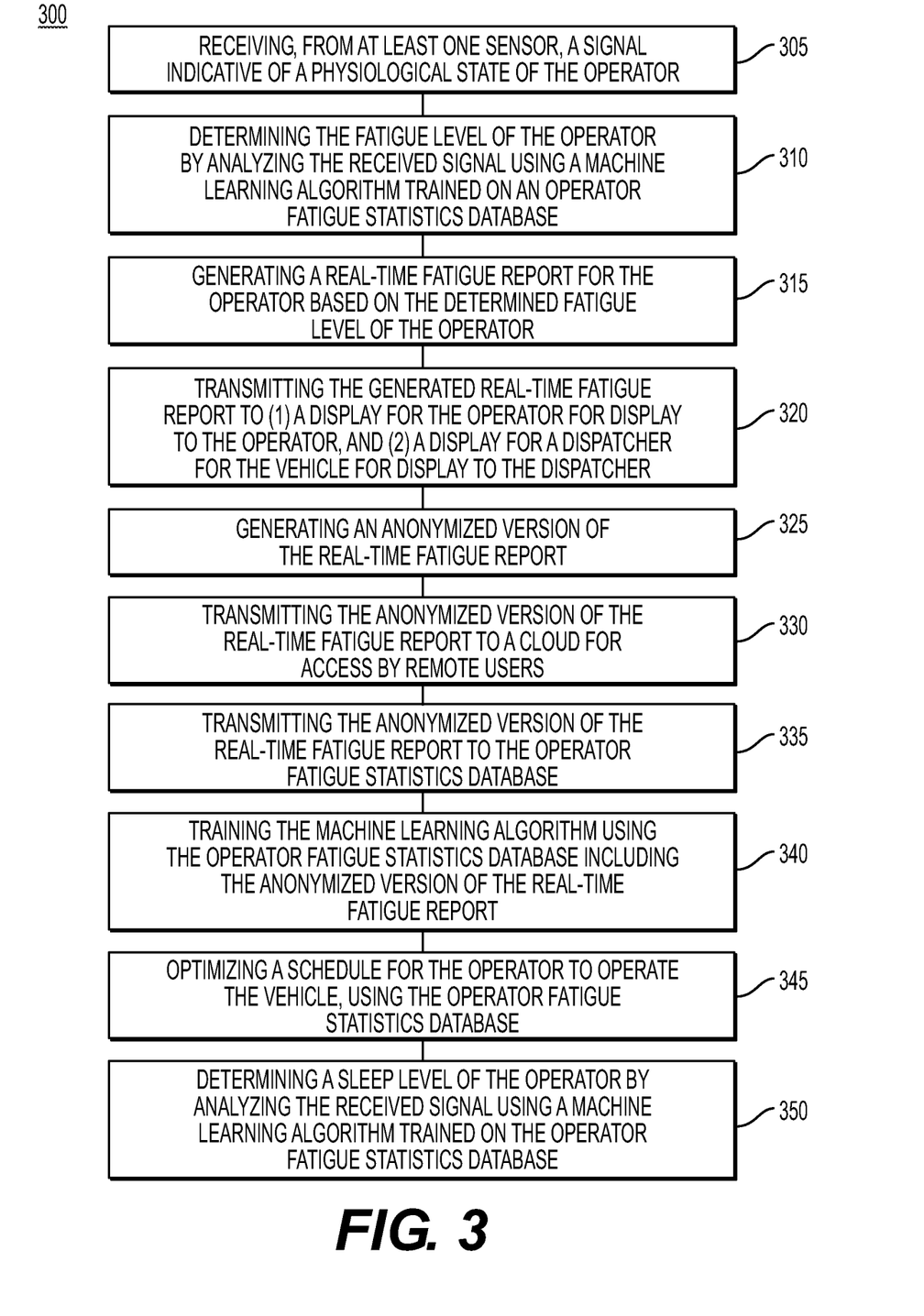
FIG. 3 depicts a flowchart of a method of monitoring and managing a fatigue level of an operator using sensors and anonymized data, according to one or more embodiments.

FIG. 3 depicts a flowchart of a method 300 of monitoring and managing a fatigue level of an operator using sensors and anonymized data, according to one or more embodiments.

Controller 105 may receive, from at least one sensor 120, a signal indicative of a physiological state of the operator 115 (operation 305). Controller 105 may determine the fatigue level of the operator 115 by analyzing the received signal using a machine learning algorithm trained on an operator fatigue statistics database (operation 310). Controller 105 may generate a real-time fatigue report for the operator 115 based on the determined fatigue level of the operator 115 (operation 315). Controller 105 may transmit the generated real-time fatigue report to (1) a display 130 for the operator 115 for display to the operator 115, and (2) a real-time dashboard 156 for a dispatcher 147 for the vehicle 110 for display to the dispatcher 147 (operation 320).

Controller 105 may generate an anonymized version of the real-time fatigue report (operation 325), and transmit the anonymized version of the real-time fatigue report to a cloud 190 for access by remote users (operation 330). The remote users may include a safety manager 145 and an operations manager 146 viewing the anonymized version of the real-time fatigue report as anonymized statistics 155 in operations center 140.

Controller 105 may transmit the anonymized version of the real-time fatigue report to the operator fatigue statistics database, which may be stored in cloud 190 (operation 335). Controller 105 may train the machine learning algorithm using the operator fatigue statistics database including the anonymized version of the real-time fatigue report (operation 340).

The anonymized version of the real-time fatigue report may be generated by controller 105 after operation of the vehicle 110 is completed by the operator 115. Controller 105 may optimize a schedule for the operator 115 to operate the vehicle 110, using the operator fatigue statistics database (operation 345).

Controller 105 may determine a sleep level of the operator 115 by analyzing the received signal using a machine learning algorithm trained on the operator fatigue statistics database (operation 350). The real-time fatigue report may include the determined sleep level of the operator 115. The fatigue level may be provided as a number from 1 to 5.

Figure 4:
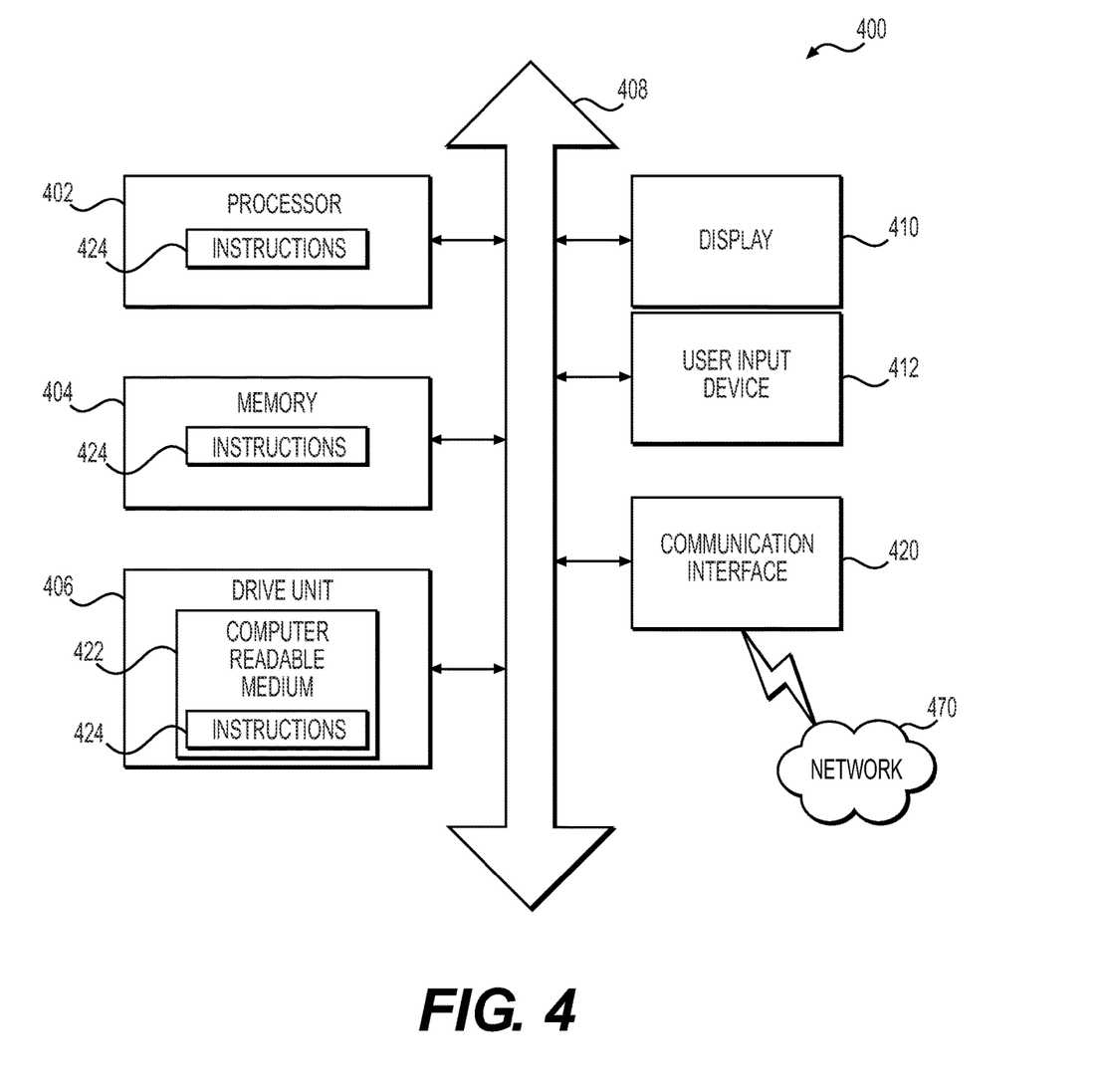
FIG. 4 depicts an implementation of a computer system that may execute techniques presented herein, according to one or more embodiments.

FIG. 4 depicts an implementation of a computer system 400 that may execute techniques presented herein, according to one or more embodiments.

The computer system 400 may include a set of instructions that can be executed to cause the computer system 400 to perform any one or more of the methods or computer based functions disclosed herein. The computer system 400 may operate as a standalone device or may be connected, e.g., using a network, to other computer systems or peripheral devices.

In a networked deployment, the computer system 400 may operate in the capacity of a server or as a client in a server-client user network environment, or as a peer computer system in a peer-to-peer (or distributed) network environment. The computer system 400 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 400 can be implemented using electronic devices that provide voice, video, or data communication. Further, while the computer system 400 is illustrated as a single system, the term "system" shall also be taken to include any collection of systems or sub-systems that individually or jointly execute a set, or multiple sets, of instructions to perform one or more computer functions.

As illustrated in FIG. 4, the computer system 400 may include a processor 402, e.g., a central processing unit (CPU), a graphics processing unit (GPU), or both. The processor 402 may be a component in a variety of systems. For example, the processor 402 may be part of a standard computer system. The processor 402 may be one or more general processors, digital signal processors, application specific integrated circuits, field programmable gate arrays, servers, networks, digital circuits, analog circuits, combinations thereof, or other now known or later developed devices for analyzing and processing data. The processor 402 may implement a software program, such as code generated manually (i.e., programmed).

The computer system 400 may include a memory 404 that can communicate via a bus 408. The memory 404 may be a main memory, a static memory, or a dynamic memory. The memory 404 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 404 includes a cache or random-access memory for the processor 402. In alternative implementations, the memory 404 is separate from the processor 402, such as a cache memory of a processor, the system memory, or other memory. The memory 404 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 404 is operable to store instructions executable by the processor 402. The functions, acts or tasks illustrated in the figures or described herein may be performed by the processor 402 executing the instructions stored in the memory 404. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 400 may further include a display 410, such as a liquid crystal display (LCD), an organic light emitting diode (OLED), a flat panel display, a solid-state display, a cathode ray tube (CRT), a projector, a printer or other now known or later developed display device for outputting determined information. The display 410 may act as an interface for the user to see the functioning of the processor 402, or specifically as an interface with the software stored in the memory 404 or in the drive unit 406.

Additionally or alternatively, the computer system 400 may include an input device 412 configured to allow a user to interact with any of the components of computer system 400. The input device 412 may be a number pad, a keyboard, or a cursor control device, such as a mouse, or a joystick, touch screen display, remote control, or any other device operative to interact with the computer system 400.

The computer system 400 may also or alternatively include drive unit 406 implemented as a disk or optical drive. The drive unit 406 may include a computer-readable medium 422 in which one or more sets of instructions 424, e.g. software, can be embedded. Further, the instructions 424 may embody one or more of the methods or logic as described herein. The instructions 424 may reside completely or partially within the memory 404 and/or within the processor 402 during execution by the computer system 400. The memory 404 and the processor 402 also may include computer-readable media as discussed above.

In some systems, a computer-readable medium 422 includes instructions 424 or receives and executes instructions 424 responsive to a propagated signal so that a device connected to a network 470 can communicate voice, video, audio, images, or any other data over the network 470. Further, the instructions 424 may be transmitted or received over the network 470 via a communication port or interface 420, and/or using a bus 408. The communication port or interface 420 may be a part of the processor 402 or may be a separate component. The communication port or interface 420 may be created in software or may be a physical connection in hardware. The communication port or interface 420 may be configured to connect with a network 470, external media, the display 410, or any other components in computer system 400, or combinations thereof. The connection with the network 470 may be a physical connection, such as a wired Ethernet connection or may be established wirelessly as discussed below. Likewise, the additional connections with other components of the computer system 400 may be physical connections or may be established wirelessly. The network 470 may alternatively be directly connected to a bus 408.

While the computer-readable medium 422 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium 422 may be non-transitory, and may be tangible.

The computer-readable medium 422 can include a solid-state memory such as a memory card or other package that houses one or more non-volatile read-only memories. The computer-readable medium 422 can be a random-access memory or other volatile re-writable memory. Additionally or alternatively, the computer-readable medium 422 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and computer systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The computer system 400 may be connected to a network 470. The network 470 may define one or more networks including wired or wireless networks. The wireless network may be a cellular telephone network, an 802.11, 802.16, 802.20, or WiMAX network. Further, such networks may include a public network, such as the Internet, a private network, such as an intranet, or combinations thereof, and may utilize a variety of networking protocols now available or later developed including, but not limited to TCP/IP based networking protocols. The network 470 may include wide area networks (WAN), such as the Internet, local area networks (LAN), campus area networks, metropolitan area networks, a direct connection such as through a Universal Serial Bus (USB) port, or any other networks that may allow for data communication. The network 470 may be configured to couple one computing device to another computing device to enable communication of data between the devices. The network 470 may generally be enabled to employ any form of machine-readable media for communicating information from one device to another. The network 470 may include communication methods by which information may travel between computing devices. The network 470 may be divided into sub-networks. The sub-networks may allow access to all of the other components connected thereto or the sub-networks may restrict access between the components. The network 470 may be regarded as a public or private network connection and may include, for example, a virtual private network or an encryption or other security mechanism employed over the public Internet, or the like.

In accordance with various implementations of the present disclosure, the methods described herein may be implemented by software programs executable by a computer system. Further, in an exemplary, non-limited implementation, implementations can include distributed processing, component/object distributed processing, and parallel processing. Alternatively, virtual computer system processing can be constructed to implement one or more of the methods or functionality as described herein.

Although the present specification describes components and functions that may be implemented in particular implementations with reference to particular standards and protocols, the disclosure is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure may be implemented using any appropriate techniques for implementing the functionality described herein. The disclosure is not limited to any particular programming language or operating system.

As is apparent from the embodiments above, an advantage to the disclosed systems and methods is for an operational center to detect severe fatigue and find a replacement operator, thus reducing significantly the inconvenience and cost. By accessing more precise information on an actual level of fatigue by the disclosed systems and methods, operators may be more likely to extend duty time in some exceptional situations when time limits would have a severe operational impact. By accessing more precise information on an actual level of fatigue by the disclosed systems and methods, operators may be more likely to realize they should stop operating a vehicle, thus avoiding a risk of accident. Additionally, by monitoring a quality of sleep by the disclosed systems and methods, resting times for operators may be optimized during long range operations, which may optimize operator usage via optimized scheduling. Embodiments above may detect, earlier than conventional systems, that an operator has reached a level of fatigue that is not sustainable. Embodiments above may predict if the operator will recover from the current level of fatigue depending on a trend determined during observation.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for monitoring a fatigue level of an operator of a vehicle, the system comprising:
    at least one sensor configured to generate a signal indicative of a physiological state of the operator, the signal being defined at least in part by operator-specific data;
    a display for the operator; and
    one or more controllers configured to:
        receive, from the at least one sensor, the signal indicative of the physiological state of the operator;
        based at least in part on the operator-specific data, determine the fatigue level of the operator by analyzing the received signal using an algorithm developed using anonymous operator fatigue statistics stored at an operator fatigue statistics database;
        based at least in part on the operator-specific data, determine a sleep level of the operator by analyzing the received signal using the algorithm developed using anonymous operator fatigue statistics stored at the operator fatigue statistics database;
        generate a real-time fatigue report for the operator based on the determined fatigue level of the operator, wherein the real-time fatigue report includes the determined fatigue level and the determined sleep level of the operator;
        transmit the generated real-time fatigue report to (1) the display for the operator for display to the operator, and (2) a display for a dispatcher for the vehicle for display to the dispatcher;
        based at least in part on the real-time fatigue report, generate an anonymized fatigue report wherein the anonymized fatigue report includes anonymous fatigue level data corresponding to an anonymized version of the determined fatigue level and anonymous sleep level data corresponding to an anonymized version of the determined sleep level, wherein the anonymous fatigue level data is not associated with the operator-specific data of the signal received from the at least one sensor, and wherein an identity of the operator is de-correlated from any associated fatigue data in the anonymized fatigue report;
        transmit the anonymized fatigue report to a cloud for access by remote users;
        transmit the anonymized fatigue report to the operator fatigue statistics database;
        train the machine learning algorithm using the operator fatigue statistics database including the anonymized fatigue report, as the algorithm;
        optimize a schedule for the operator to operate the vehicle, using the operator fatigue statistics database;
        wherein the anonymized fatigue report is generated after operation of the vehicle is completed by the operator.

2. The system of claim 1, wherein the fatigue level is provided as a number from 1 to 5.

3. A method for monitoring a fatigue level of an operator of a vehicle, the method comprising:
    performing, by one or more controllers, operations including:
        receiving, from at least one sensor, a signal indicative of a physiological state of the operator, the signal being defined at least in part by operator-specific data;
        based at least in part on the operator-specific data, determining the fatigue level of the operator by analyzing the received signal using an algorithm developed using anonymous operator fatigue statistics stored at an operator fatigue statistics database;
        based at least in part on the operator-specific data, determine a sleep level of the operator by analyzing the received signal using the algorithm developed using anonymous operator fatigue statistics stored at the operator fatigue statistics database;
        generating a real-time fatigue report for the operator based on the determined fatigue level of the operator, wherein the real-time fatigue report includes the determined fatigue level and the determined sleep level of the operator;
        transmitting the generated real-time fatigue report to (1) the display for the operator for display to the operator, and (2) a display for a dispatcher for the vehicle for display to the dispatcher;
        based at least in part on the real-time fatigue report, generating an anonymized-fatigue report wherein the anonymized fatigue report includes anonymous fatigue level data corresponding to an anonymized version of the determined fatigue level and anonymous sleep level data corresponding to an anonymized version of the determined sleep level, wherein the anonymous fatigue level data is not associated with the operator-specific data of the signal received from the at least one sensor, and wherein an identity of the operator is de-correlated from any associated fatigue data in the anonymized fatigue report;
        transmitting the anonymized fatigue report to a cloud for access by remote users;
    transmit the anonymized fatigue report to the operator fatigue statistics database;
        training the machine learning algorithm using the operator fatigue statistics database including the anonymized fatigue report, as the algorithm;
        optimizing a schedule for the operator to operate the vehicle, using the operator fatigue statistics database;
        wherein the anonymized fatigue report is generated after operation of the vehicle is completed by the operator.

4. The method of claim 3, wherein the fatigue level is provided as a number from 1 to 5.

5. A non-transitory computer-readable medium storing instructions, that when executed by one or more controllers, perform a method for monitoring a fatigue level of an operator of a vehicle, the method comprising:
    receiving, from at least one sensor, a signal indicative of a physiological state of the operator, the signal being defined at least in part by operator-specific data;
    based at least in part on the operator-specific data, determining the fatigue level of the operator by analyzing the received signal using an algorithm developed using anonymous operator fatigue statistics stored at an operator fatigue statistics database;

based at least in part on the operator-specific data, determine a sleep level of the operator by analyzing the received signal using the algorithm developed using anonymous operator fatigue statistics stored at the operator fatigue statistics database;

generating a real-time fatigue report for the operator based on the determined fatigue level of the operator, wherein the real-time fatigue report includes the determined fatigue level and the determined sleep level of the operator;

transmitting the generated real-time fatigue report to (1) the display for the operator for display to the operator, and (2) a display for a dispatcher for the vehicle for display to the dispatcher;

based at least in part on the real-time fatigue report, generating an anonymized-fatigue report wherein the anonymized fatigue report includes anonymous fatigue level data corresponding to an anonymized version of the determined fatigue level and anonymous sleep level data corresponding to an anonymized version of the determined sleep level, wherein the anonymous fatigue level data is not associated with the operator-specific data of the signal received from the at least one sensor, and wherein an identity of the operator is de-correlated from any associated fatigue data in the anonymized fatigue report;

transmitting the anonymized fatigue report to a cloud for access by remote users;

transmit the anonymized fatigue report to the operator fatigue statistics database;

training the machine learning algorithm using the operator fatigue statistics database including the anonymized fatigue report, as the algorithm;

optimizing a schedule for the operator to operate the vehicle, using the operator fatigue statistics database;

wherein the anonymized fatigue report is generated after operation of the vehicle is completed by the operator.

6. The non-transitory computer-readable medium of claim 5, wherein the real-time fatigue report includes the determined sleep level of the operator provided as a number from 1 to 5.

* * * * *